United States Patent
Durham et al.

(10) Patent No.: US 10,726,152 B1
(45) Date of Patent: Jul. 28, 2020

(54) COMPUTING SYSTEM THAT FACILITATES DIGITAL RIGHTS MANAGEMENT FOR HEALTHCARE RECORDS

(71) Applicant: Allscripts Software, LLC, Raleigh, NC (US)

(72) Inventors: Ryan Durham, Litchfield, IL (US); Stephen Anthony Canzano, Cape Coral, FL (US); Scott Alan Mueller, Glen Carbon, IL (US); Jonathan Edward Blankenship, Springfield, IL (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 326 days.

(21) Appl. No.: 15/910,553

(22) Filed: Mar. 2, 2018

(51) Int. Cl.
    *G06F 21/62* (2013.01)
    *G16H 10/20* (2018.01)
    *H04L 29/06* (2006.01)

(52) U.S. Cl.
    CPC ...... *G06F 21/6245* (2013.01); *G06F 21/6263* (2013.01); *G16H 10/20* (2018.01); *H04L 63/10* (2013.01); *H04L 2463/121* (2013.01)

(58) Field of Classification Search
    CPC .................................................. G06F 21/6245
    See application file for complete search history.

(56) References Cited

U.S. PATENT DOCUMENTS

| | | | | |
|---|---|---|---|---|
| 8,407,081 | B1* | 3/2013 | Rajasenan | G06Q 10/0637 705/7.42 |
| 10,169,607 | B1* | 1/2019 | Sheth | G06F 21/6245 |
| 10,417,380 | B1* | 9/2019 | Kaye | G16H 10/60 |
| 2012/0179908 | A1* | 7/2012 | Duma | G16H 10/65 713/165 |
| 2012/0260094 | A1* | 10/2012 | Asim | G06F 21/10 713/171 |
| 2013/0117313 | A1* | 5/2013 | Miao | G06F 21/6227 707/781 |
| 2015/0025329 | A1* | 1/2015 | Amarasingham | G16H 40/67 600/301 |
| 2015/0213195 | A1* | 7/2015 | Blechman | G16H 10/60 705/51 |
| 2015/0227756 | A1* | 8/2015 | Barbas | G06F 16/2457 707/783 |
| 2016/0132645 | A1* | 5/2016 | Charpentier | G16H 10/60 705/3 |

* cited by examiner

*Primary Examiner* — Lynn D Feild
*Assistant Examiner* — Viral S Lakhia
(74) *Attorney, Agent, or Firm* — Medley, Behrens & Lewis, LLC (57) ABSTRACT

Described herein are various technologies pertaining to facilitating digital rights management of patient healthcare records. A computing system executing an electronic health records application (EHR) receives an attribute of a healthcare worker and a patient identifier from a client computing device. The computing system retrieves a computer-readable file for the patient, the computer-readable file comprising a plurality of file records and a file access portion. A file record in the plurality of file records comprises a data portion and an access portion. The computing system transmits data in the data portion to the client computing device only when both the file access portion of the computer-readable file and the access portion of the file record include the attribute of the healthcare worker.

18 Claims, 8 Drawing Sheets

COMPUTING SYSTEM THAT FACILITATES DIGITAL RIGHTS MANAGEMENT FOR HEALTHCARE RECORDS

BACKGROUND

Electronic health record (EHR) systems are systems utilized by healthcare organization to generate and maintain health records for patients. As a patient visits different healthcare organizations using different EHR systems, his or her medical records become scattered across various EHR systems. This leads to "silos" of health data for the patient that can be difficult to access. For instance, a patient may make an emergency room visit, and a hospital system that operates the emergency room may use a first EHR system to generate and maintain patient records. Sometime thereafter, the patient may visit an orthopedic surgery center, where the center utilizes a second EHR system to generate and maintain patient records. Conventionally, a healthcare worker at the orthopedic surgery center is unable to access the records about the patient generated and stored by the first EHR system. Instead, the healthcare worker must contact the hospital that operates the emergency room, whereupon the hospital will provide a summary of a patient record of interest to the healthcare worker at the orthopedic surgery center (presuming that the patient consented to the sharing of the patient record).

Conventional EHR systems are not well suited for granular digital rights management (DRM). More specifically, conventional EHRs store data in conformance with data structures designed decades ago when digital rights management was not a priority to designers of electronic health records. Moreover, any DRM restrictions assigned to a conventional electronic health record tend not to follow the electronic health record as it is transferred across EHRs. In an example, the patient may wish that a first healthcare worker (e.g., a clinician) be provided with access to a first portion of his or her health record, but not a second portion. Likewise, the patient may wish that a second healthcare worker be provided with access to the second portion of his or her health record, but not the first portion. Even if the EHR were to support these DRM restrictions, if the patient were to change healthcare providers (or if the healthcare enterprise were to change its EHR), the DRM restrictions would not follow the health records of the patient.

SUMMARY

The following is a brief summary of subject matter that is described in greater detail herein. This summary is not intended to be limiting as to the scope of the claims.

Described herein are various technologies pertaining to facilitating digital rights management (DRM) for electronic healthcare records. More specifically, the technologies described herein facilitate DRM through use of an electronic health records application (EHR) architecture where multiple instances of an EHR, used by several healthcare enterprises, may have access to a single electronic health record of a patient. Additionally, the technologies described herein facilitate DRM through use of a data structure for the electronic health record which allows for DRM restrictions to be granularly assigned throughout the electronic health record, wherein such DRM restrictions are maintained across several healthcare enterprises.

A server computing device executing an EHR receives at least one attribute of a healthcare worker operating a client computing device. The client computing device executes a client electronic health records application (client EHR). For instance, the at least one attribute of the healthcare worker can include an identifier for the healthcare worker and/or an identifier for a healthcare organization to which the healthcare worker belongs. Subsequently, the server computing device receives a patient identifier for a patient from the client computing device. Responsive to receiving the patient identifier, the EHR retrieves a computer-readable file for the patient by executing a search over a data store comprising a plurality of computer-readable files, each file in the plurality of computer-readable files corresponding to a patient.

The computer-readable file for the patient comprises a plurality of file records and a file access portion. The computer-readable file for the patient may also comprise a map portion and a read model. It is contemplated that the plurality of file records may encompass all or most of the healthcare records of the patient. A file record in the plurality of file records comprises a data portion and an access portion. Access to data in the data portion is restricted to healthcare workers who have the attribute in the access portion. For instance, the attribute in the access portion may be an identifier for the healthcare worker and/or an identifier for a healthcare organization to which the healthcare worker belongs. The file record may also comprise a marker that indicates a beginning of the file record, a pointer portion that can be populated with pointers to child file records within the computer-readable file for the patient, and a checksum. The map portion of the computer-readable file may include a timestamp indicative of when the file record was created. Access to the computer-readable file as a whole is restricted to healthcare workers who have the attribute in the file access portion of the computer-readable file. The file access portion may also comprise a date associated with the attribute in the access portion of the file record and/or the attribute in the file access portion. The attribute in the access portion of the file record and the attribute in the file access portion of the computer-readable file may vary such that a healthcare worker may access some, but not all of the file records within the computer-readable file.

Responsive to retrieving the computer-readable file for the patient, the EHR compares the at least one attribute of the healthcare worker with the attribute in the file access portion and the at least one attribute of the healthcare worker with the attribute in the access portion of the file record. The EHR transmits the data portion of the file record to the client computing device only when the file access portion of the computer-readable file and the access portion of the file record within the computer-readable file include the at least one attribute of the healthcare worker. Furthermore, the EHR can be configured to transmit the data portion of the file record to the client computing device only when the date is before the timestamp. Likewise, the EHR can be configured to transmit the data portion of the file record to the client computing device only when the date is after the timestamp.

The above-described technologies present various advantages over conventional EHRs. First, by keeping the healthcare records of the patient in a single computer-readable file, the problem of "silos" is alleviated as the entirety of (or most of) the healthcare records of the patient can be found in a single place. Second, through use of the access portion and file access portion, the above-described technologies enable a patient to restrict access to certain health care records to designated individuals and/or organizations.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Various technologies pertaining to facilitating digital rights management for healthcare records are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

Figure 1:
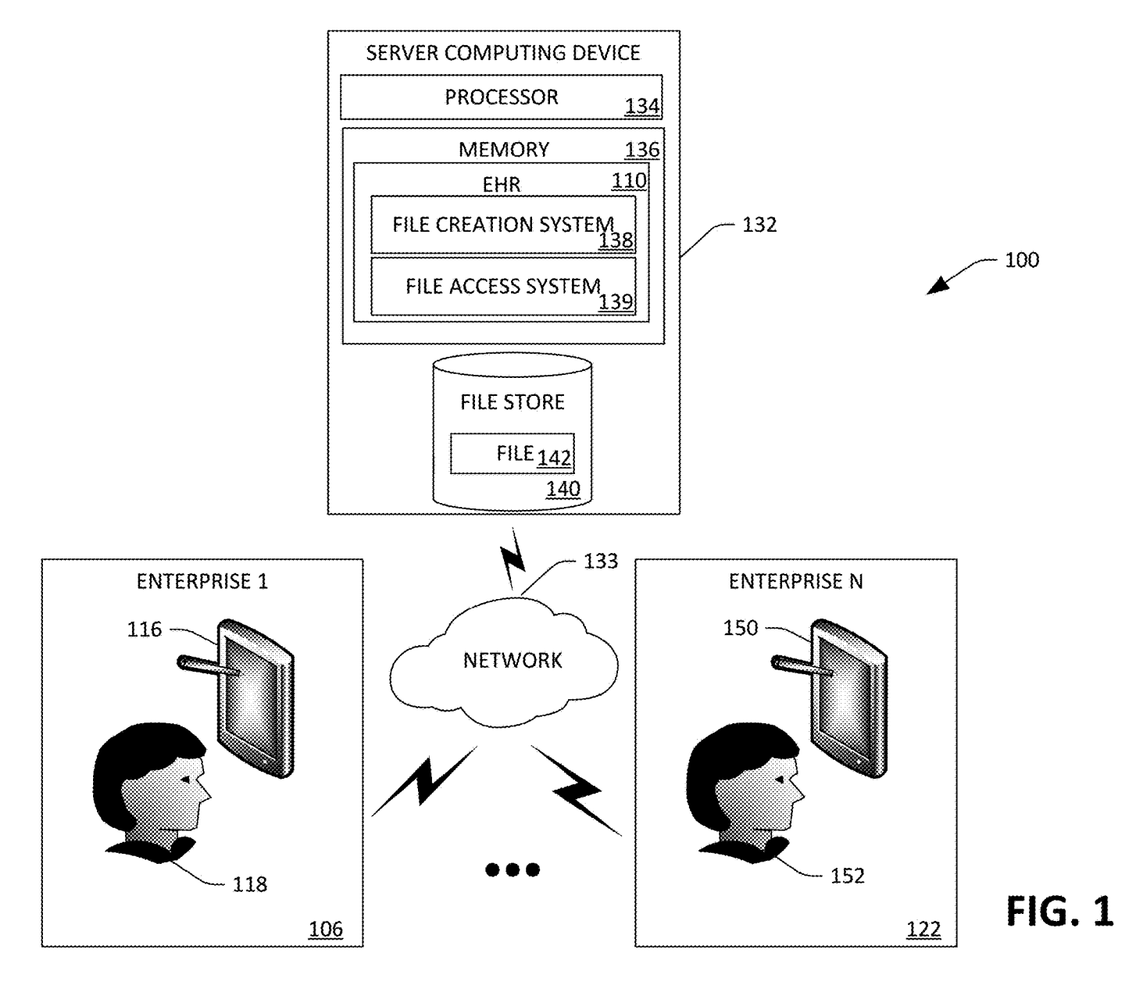
FIG. 1 is a functional block diagram of an exemplary computing system that facilitates digital rights management of healthcare records.

With reference to FIG. 1, an exemplary computing system 100 that facilitates digital rights management for healthcare records is illustrated. The computing system 100 can include a server computing device 132. The server computing device 132 includes a processor 134 and memory 136, wherein the memory 136 includes an electronic health records application (EHR) 110 loaded therein. Generally, the EHR 110 is configured to facilitate creation, storage, and maintenance of electronic health records for patients. As such, the EHR 110 comprises a file creation system 138 and a file access system 139. In general, the file creation system 138 is tasked with creating a computer-readable file for a patient. The file access system 139 is configured to ensure that data in the computer-readable file can only be accessed by healthcare workers who possess the requisite permission. The server computing device 132 additionally comprises a file store 140 that includes a computer-readable file 142 for a patient, wherein the EHR 110 has access to the file store 140. While the file store 140 is illustrated as including a single computer-readable file, it is understood that the file store 140 can include (separate) files for many different patients.

The computing system 100 may further include a first client computing device 116 operated by a healthcare worker 118 in a first enterprise 106. In an example, the first enterprise 106 may be a first healthcare organization, and can be or manage a hospital, an urgent care facility, a family doctor facility, etc. The first client computing device 116 is in communication with the server computing device 132 by way of a network 133 (e.g., the Internet). The first client computing device 116 is employed by the healthcare worker 118 to access the EHR 110. For instance, the first client computing device 116 may have a client EHR application installed thereon that interfaces with the EHR 110, wherein data can be transmitted between the client EHR and the EHR 110 to: 1) create and/or modify health records for a patient; and/or 2) retrieve information (e.g., files records within files, etc.) from the file store 140. For example, the healthcare worker 118 can utilize the first client computing device 116 to set forth notes pertaining to a patient encounter, and the notes can be transmitted to the server computing device 132, wherein the EHR 110 can incorporate the notes into the computer-readable file 142.

The computing system 100 may also include an nth client computing device 150 operated by a second healthcare worker 152 in an nth enterprise 122. In an example, the nth enterprise 122 may be a healthcare organization, and can be or manage a hospital, an urgent care facility, a family doctor facility, etc. The nth client computing device 150 is in communication with the server computing device 132 by way of the network 133. The nth client computing device 150 is employed by the second healthcare worker 152 to access the EHR 110. For instance, the nth client computing device 150 may have a client EHR application installed thereon that interfaces with the EHR 110, wherein data can be transmitted between the client EHR and the EHR 110 to: 1) create and/or modify health records for a patient; and/or 2) retrieve health records from the file store 140. For example, the healthcare worker 152 can utilize the nth client computing device 150 to enter thermometer readings taken over a range of time, and the thermometer readings can be transmitted to the server computing device 132, wherein the EHR 110 can incorporate the thermometer readings into the computer-readable file 142.

While the computing system 100 is depicted as both client computing device 116 and 150 having access to the EHR 110, there are other architectures contemplated. For example, the server computing device 132 (or a collection of server computing devices) can execute separate instance of the EHR 110 for each enterprise—thus, the first client computing device 116 interfaces with a first instance of the EHR executing on the server computing device 132, while the nth client computing device interfaces with an nth instance of the EHR executing on the server computing device 132. In an exemplary implementation, these instances of the EHR may executed in different virtual machines. In other examples, the instances of the EHR can be executed separately without requiring different virtual machines. For purposes of ease of explanation, the client computing devices 116 and 150 will be described as accessing the EHR 110; it is to be understood, however, that in practice the client computing device 116 and 150 will access and interact with different instances of the EHR 110.

Figure 2:
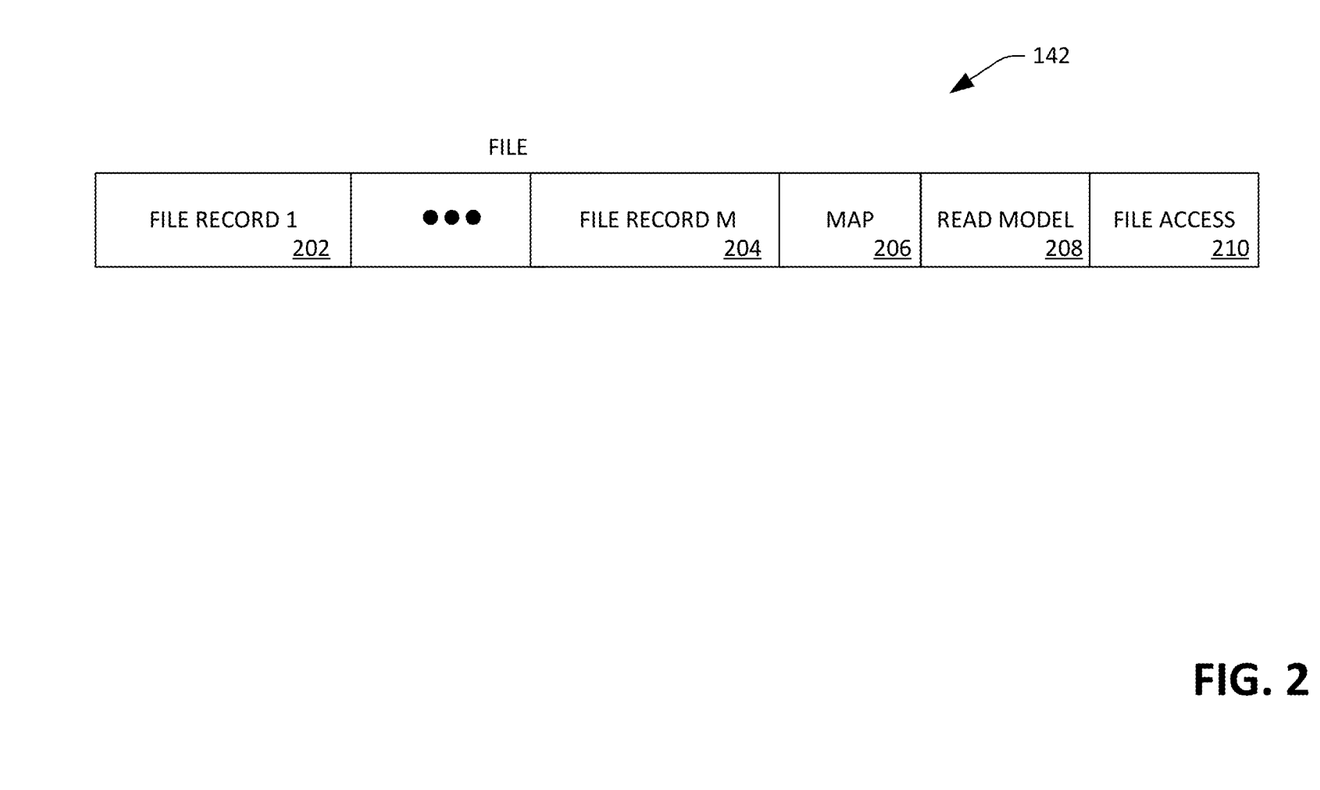
FIG. 2 is a schematic of an exemplary computer-readable file.

Referring now to FIG. 2, an exemplary schematic of the computer-readable file 142 is depicted. The computer-readable file 142 comprises a plurality of file records 202-204 that are appended to one another. The file records 202-204 are arranged in the computer-readable file 142 based upon when patient data was generated by the EHR 110. More specifically, the first file record 202 corresponds to first patient encounter data, while the mth file record 204 corresponds to mth patient encounter data that was created subsequent to the first patient encounter data. Therefore, the file records 202-204 are arranged in the computer-readable file 142 from oldest (at a beginning of the computer-readable file 142) to newest (at an end of the computer-readable file 142). Modification of the file records 202-204 is accomplished by identifying parent file records in the computer-readable file for new data received by the server computing device 132, appending additional file records reflective of the new data to the computer-readable file 142, and updating pointer portions of the file records 202-204 to include pointers to the additional file records.

The computer-readable file 142 further comprises a map portion 206 (described in greater detail below) that is appended to the mth (last) file record 204 in the computer-readable file 142. The map portion 206 identifies locations of the file records 202-204 in the computer-readable file 142. The computer-readable file 142 also comprises a read model 208 that is appended to the map portion 206. The EHR 110 can utilize the read model 208 to optimize retrieval of file records within the computer-readable file 142.

Furthermore, the computer-readable file 142 comprises a file access portion 210 appended to the read model 208. The file access portion 210 includes at least one attribute for healthcare workers that have permission to access the computer-readable file 142. In an embodiment, the file access portion 210 can identity one or more healthcare workers, wherein one or more healthcare workers are able to access the file 142. In another embodiment, the file access portion 210 can identify one or more enterprises, wherein employees in such enterprise(s) are able to access the file 142. The file access portion 210 can also include dates associated with the attribute in the file access portion 210. As will be described in greater detail below, the EHR 110 can compare a timestamp of a file record to a date included in the file access portion 210, and in an example, transmit the file record only when the date in the file access portion 210 is chronologically after the timestamp.

Figure 3:
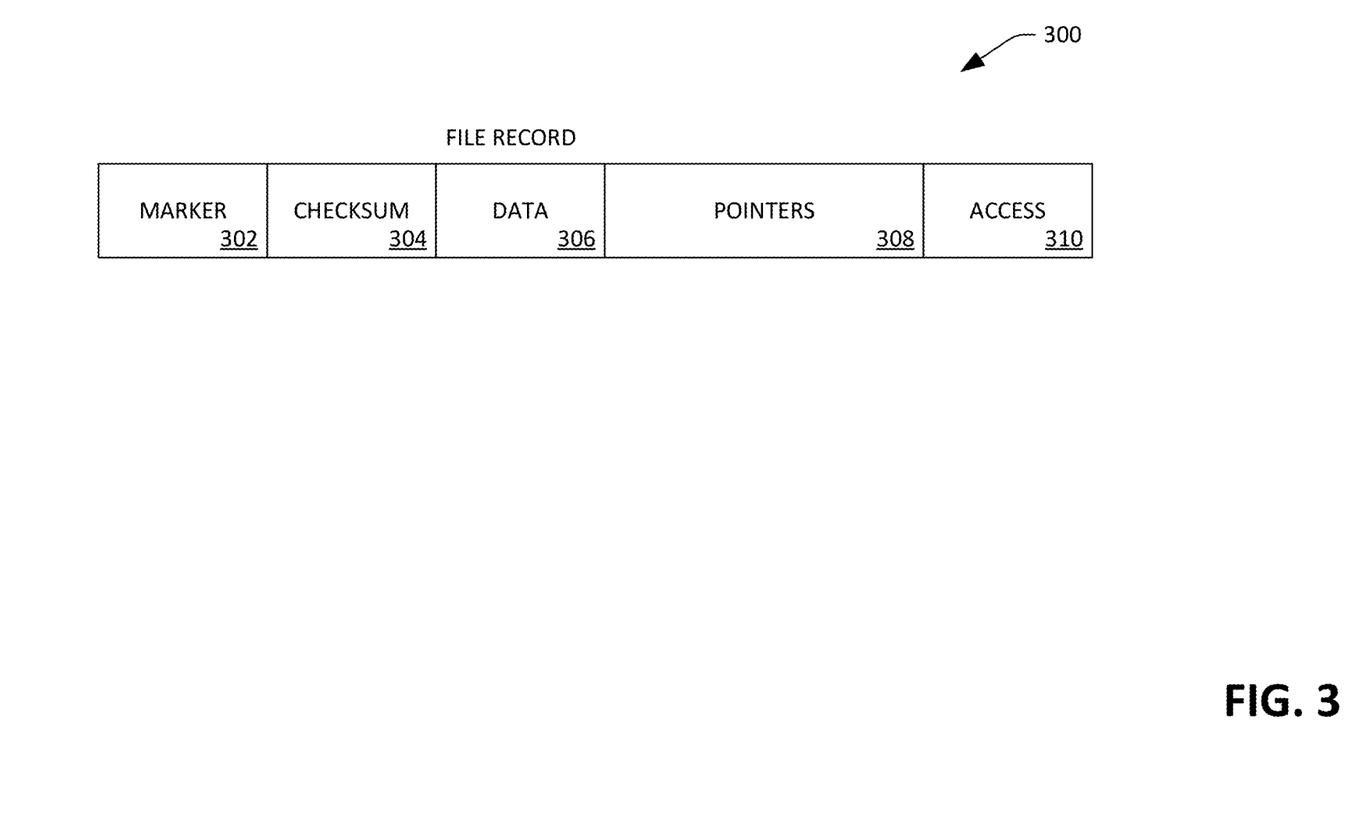
FIG. 3 is a schematic of an exemplary file record in a computer-readable file.

Now referring to FIG. 3, a schematic of an exemplary file record 300 that can be included in the computer-readable file 142 is illustrated. The file record 300 comprises data 306 about a patient encounter. The file record 300 additionally comprises a pointer portion 308. The pointer portion 308 is an area reserved for pointers to child file records of the file record 300 within the computer-readable file 142. When the file record 300 is initially created and appended to the computer-readable file 142, the pointer portion 308 does not yet contain pointers. However, as additional file records related to the data 306 are added to the computer-readable file 142, the file creation system 138 can update the pointer portion 308 to include pointers to the additional file records.

The file record 300 may also comprise a checksum 304 for the file record 300, where the checksum is over at least the data 306. Generally, the checksum 304 is used when the computer-readable file 142 is read to ensure lack of corruption of the computer-readable file 142. Additionally, the checksum 306 can further be used to skip file records when the computer-executable 142 is read by a computer-processor. The file record 300 also comprises a marker 302, wherein the marker 302 indicates a beginning of the file record 300.

Furthermore, the file record 300 comprises an access portion 310. The access portion 310 comprises one or more attributes of healthcare workers that have permission to access the data 306. In an embodiment, the attribute in the access portion 310 of the file record 300 can be an identifier for a healthcare worker. In another embodiment, the attribute in the access portion 310 of the file record 300 can be an identity of a healthcare organization. The attribute in the access portion 310 of the file record 300 may be the same as or different than the attribute in the file access portion 210 of the computer-readable 142.

Figure 4:
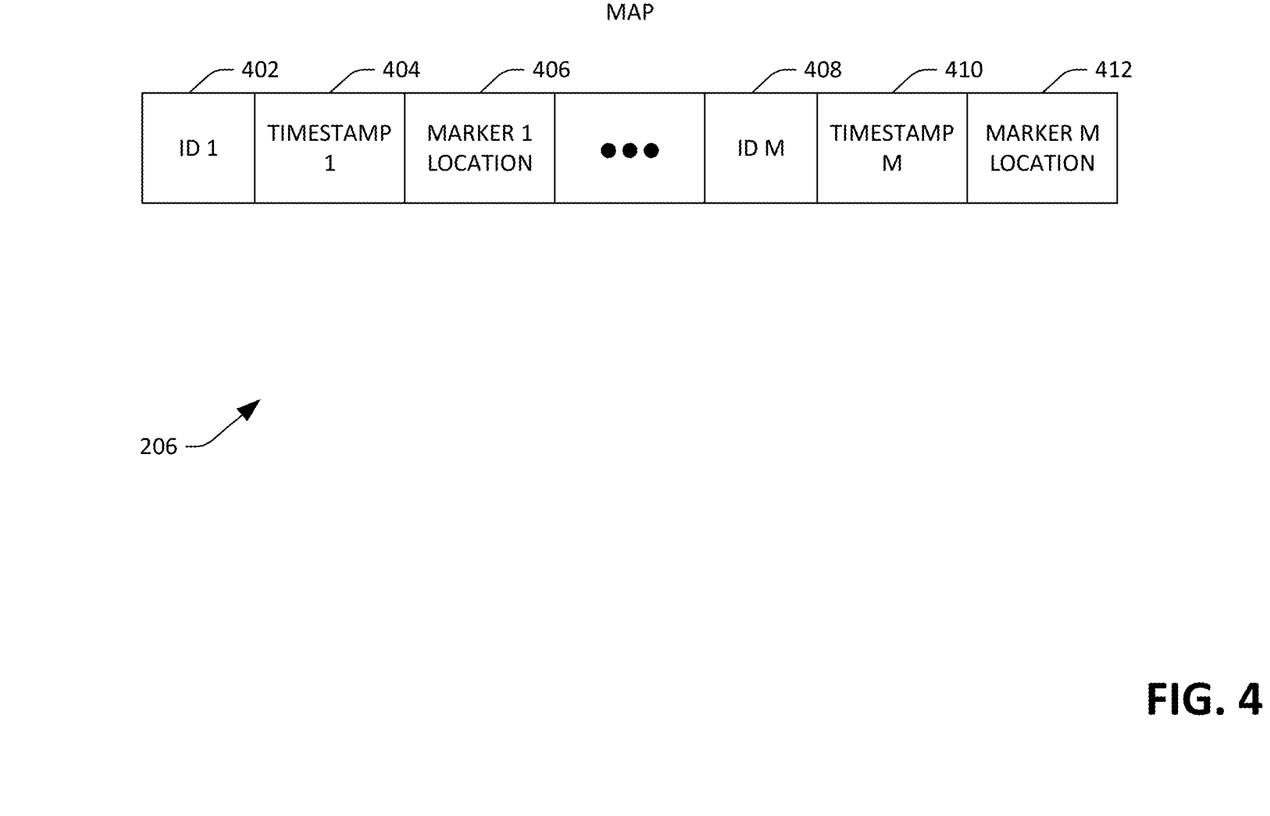
FIG. 4 is a schematic of a map portion of the computer-readable file shown in FIG. 2.

With reference to FIG. 4, a schematic of the map portion 206 of the computer-readable file 142 is illustrated. The map portion 206 includes an identifier 402 of the first file record 202, a timestamp 404 corresponding to when the first file record 202 was created, and a location 406 of the marker for the first file record 202. The map portion also includes an identifier 408 of the mth file record 204, a timestamp 410 corresponding to when the mth file record 204 was created, and a location 412 of the marker for the mth file record 204.

Figure 5:
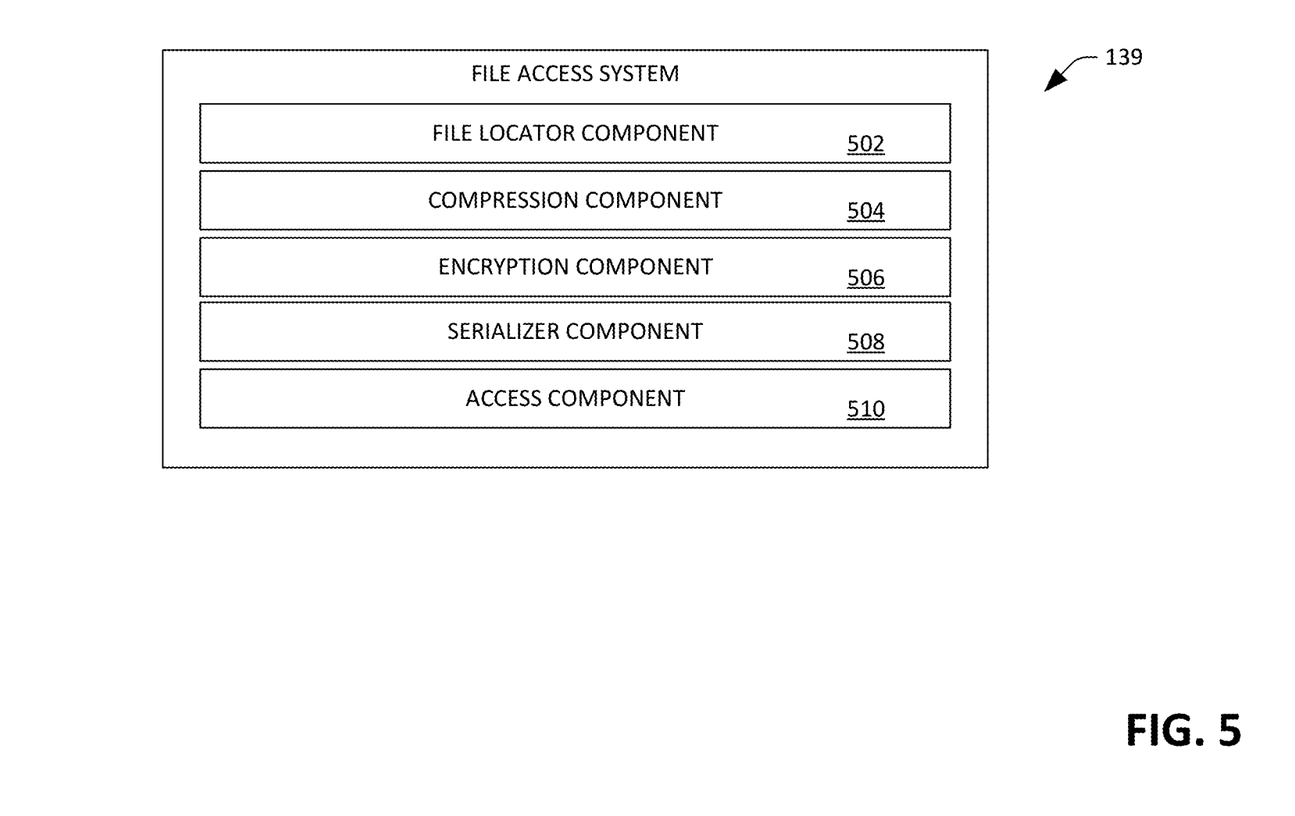
FIG. 5 is a functional block diagram of an exemplary file access system.

Turning now to FIG. 5, a functional block diagram of the exemplary file access system 139. The file access system 139 includes a file locator component 502 that is configured to search the file store 140 for a computer-readable file for a patient in response to receiving the patient identifier from one of the client computing devices 116 or 150. When the file locator component 502 is unable to locate a computer-readable file for the patient, the file creation system 138 can create a new computer-readable file for the patient.

The file access system 139 optionally also includes a compression component 504 that is configured to compress/decompress computer-readable files. For example, the computer-readable files in the file store 140 may be compressed. Therefore, when the file locator component 502 identifies that a computer-readable file exists for the patient in the file store 140, the compression component can decompress the computer-readable file such that the computer-readable file can be read by the EHR. The file access system 139 may also include an encryption component 506 that is configured to encrypt/decrypt computer-readable files. Computer-readable files in the file store 140 may be encrypted, hence, when the file locator component 502 determines that a computer-readable file exists for the patient, the encryption component 506 can decrypt the computer-readable file such that the computer-readable file can be read by the EHR. Furthermore, the file access system 139 can include a serializer component 508 that is configured to serialize/deserialize data. For example, computer-readable files in the file store 140 may be serialized for storage purposes. When the file locator component 502 determines that a computer-readable file exists for the patient (and subsequent to the computer-readable file being decompressed and/or decrypted), the serializer component 508 can deserialize the computer-readable file.

The file access system 139 also includes an access component 510. The access component 510 is designed to compare at least one attribute of a healthcare worker received from a client computing device to attributes in the file access portion of the computer-readable file and attributes in the access portion of a file record. When both the file access portion of the computer-readable file and the access portion of the file record include the at least one attribute of the healthcare worker, the access component 510 allows the file access system 139 to access and transmit the data portion of the file record to a client computing device. The access component 510 may also compare a timestamp of a file record included in the map portion of the computer-readable file to a date associated with an attribute included in the file access portion in order to determine whether or not a healthcare worker has permission to access a file record within the computer-readable file.

Exemplary operation of the computing system 100 is now set forth. In an example, when a patient first visits the enterprise 106, a healthcare worker (e.g., the healthcare worker 118) can cause a computer-readable file 142 for the patient to be created in the file store 140. For instance, the healthcare worker 118 can enter identifying information and demographic information about the patient into a graphical user interface of the client EHR at the client computing device 116, such as name, date of birth, address, gender, and so forth. The client computing device 116 transmits this information to the EHR 110 executing on the server computing device 132, and the file creation system 138 creates the computer-readable file 142 for the patient in response to receiving such information from the client computing device 116. The newly created computer-readable file 142 includes an identifier for the patient (such as a medical record number) and a pointer portion that can be later populated with pointers to file records within the computer-readable file 142 as new file records are added to the computer-readable file 142. The computer-readable file 142 may also include a map, a read model, and a file access portion. Subsequent to creation of the computer-readable file 142, it is contemplated that file records reflective of additional patient encounters are appended to the computer-readable file 142. Importantly, each file record appended to the computer-readable file 142 includes an access portion. The access portion of a file record includes at least one attribute of a healthcare worker that has permission to access data in the file record. It is understood that different file records may have different attributes in their respective access portions such that the healthcare worker 118 may have access to some, but not all, of the file records in the computer-readable file 142. Additionally, as file records are appended to the computer-readable file 142, the file creation system 138 modifies the map portion 206 of the file record to include identifiers for file records, timestamps for file records, and markers for beginnings of file records.

Sometime later, it is contemplated that the healthcare worker 118 (or some other healthcare worker) wishes to view at least a portion of the file records in the computer-readable file 142. For example, the healthcare worker 118 may wish to examine the medical history of the patient contained in the computer-readable file in order to treat/diagnose the patient. The first client computing device 116 can receive input indicative of at least one attribute of the healthcare worker 118. More specifically, the first client computing device 116 can receive credentials from the healthcare worker 118. The EHR 110 can then authenticate the healthcare worker 118, and can provide the healthcare worker 118 with access to the functionality of the EHR 110 via the client EHR executing on the first client computing device 116. In a non-limiting example, the at least one attribute patient can be an identifier for the healthcare worker 118 or an identity of the first enterprise 106. In an embodiment, the EHR 110 may receive user credentials from the first client computing device 116, and, based on the user credentials, the EHR 110 may retrieve additional attributes for the healthcare worker 118 based on the received credentials (e.g., by executing a search over a data store). The first client computing device 116 may then receive a patient identifier (e.g., a medical record number) for the patient as input from the healthcare worker 118. The first client computing device 116 can then transmit the patient identifier to the server computing device 132 executing the EHR 110.

Responsive to receiving the patient identifier, the EHR 110 may then retrieve the computer-readable file 142 for the patient by executing a search over the data store 140 based on the patient identifier. As discussed above, the computer-readable file 142 comprises a plurality of file records and a file access portion. Each file record in the plurality of file records is reflective of a patient encounter and comprises data about the patient and an access portion. The access portion of a file record includes at least one attribute of a healthcare worker 118 that has permission to access the file record. If the computer-readable file 142 is encrypted, compressed, and/or serialized, the EHR 110 may decrypt, decompress, and/or deserialize the file.

The EHR 110 then compares the at least one attribute of the patient received from the first client computing device 116 to the attribute in file access portion of the computer-readable file 142 to determine whether the file access portion includes the at least one attribute for the healthcare worker 118. In an embodiment, when the file access portion does not include the at least one attribute of the healthcare worker 118, the EHR 110 can transmit a message to the first client computing device 116 indicating that the healthcare worker 118 does not have permission to access the computer-readable file 142.

The EHR 110 also compares the at least one attribute of the patient to the attribute in the access portion of each file record in the plurality of file records. The EHR 110 transmits data portions of file records only when the corresponding access portion in the file records includes the at least one attribute of the healthcare worker 118 received from the first client computing device 116. In an example, the file access portion of the computer-readable file 142 and the access portion of the file record within the computer-readable file 142 both include the at least one attribute for the healthcare worker 118 and thus the EHR 110 transmits the data portion of the file record to the first client computing device 116. As the attributes in the file access portions may vary, it is contemplated that some of the data in the computer-readable file 142 may not be transmitted to the first client computing device 116. For example, if the computer-readable file 142 comprises a first file record with a first attribute in its access portion and a second file record with a second attribute in its access portion, and the at least one attribute of the healthcare worker includes the first attribute, but not the second attribute, the EHR 110 will transmit the data portion of the first file record to the first client computing device 116, but not the data portion of the second file record.

In an embodiment, when an access portion of a file record does not include the at least one attribute of the healthcare worker 118, the EHR 110 can be configured to transmit a message to the first client computing device 116 indicating that access to the file record is restricted for the healthcare worker 118. The healthcare worker 118 and the patient may then confer, and in an example, the patient may decide to give the healthcare worker 118 access to the file record in the computer-readable file 142. The first client computing device 116 can receive input indicating that the patient has agreed to give the healthcare worker 118 access to the file record. Responsive to receiving the input, the first client computing device 116 can transmit the input to the EHR 110, wherein the file creation system 138 can modify the access portion of the file record to include an attribute of the healthcare worker 118.

Likewise, the patient may decide to make accessing the file more restrictive. In an example, the access portion of the file record includes a first attribute and a second attribute. The first client computing device 116 can receive input indicating that healthcare workers having the second attribute should no longer be allowed to access the file record. Responsive to receiving the input, the first client computing device 116 can transmit data indicative of the aforementioned access restrictions to the EHR 110, wherein the file creation system 138 can remove the second attribute in the access portion of the file record.

In another embodiment, when the access portion of the file record does not include the at least one attribute of the healthcare worker 118, the EHR 110 can be configured to fail to give an indication that access to the file record has been restricted. Thus, in this embodiment, the healthcare worker 118 will be unaware of any file records in the computer-readable file 142 that he or she cannot access.

In an embodiment, the EHR 110 may also restrict access to certain file records based on time. As noted above, when a file record is appended to the computer-readable file 142, the map portion 206 is modified to include a timestamp indicative of when the file record was created. In this embodiment, the file access portion and/or an access portion of the file record also includes a date associated with the attribute of the healthcare worker 118 in the file access portion and/or access portion of the file record. In addition to comparing the at least one attribute of the healthcare worker 118 to the attribute in the access portion and file access portion, the EHR 110 also compares the date in the access portion and/or file access portion to the timestamp of the file record in the map portion 206. The EHR 110 transmits the data portion of the file record only when the date is chronologically before the timestamp. In another embodiment, the EHR 110 can be configured to transmit the data portion of the file record only when the date is chronologically after the timestamp.

In a further example, the patient may visit the enterprise 122 after the visit to the first enterprise 106 and the second healthcare worker 152 may wish to view at least a portion of the file records in the computer-readable file 142. The second client computing device 150 transmits an attribute of the second healthcare worker 152 and an identifier for the patient to the server computing device 132. The patient may not want the second healthcare worker 152 to have access to the data in the file record described above. Accordingly, while the file access portion of the computer-readable file 142 includes the attribute of the second healthcare worker 152, the access portion of the file record does not. As the at least one attribute of the second healthcare worker 152 received from the second client computing device 150 fails to include the attribute in the access portion of the above described file record, the EHR 110 will not transmit the file record to the second client computing device 150. However, the EHR 110 will transmit other file records in the plurality of file record that include the attribute of the second healthcare worker 152 in their access portions.

Figure 6:
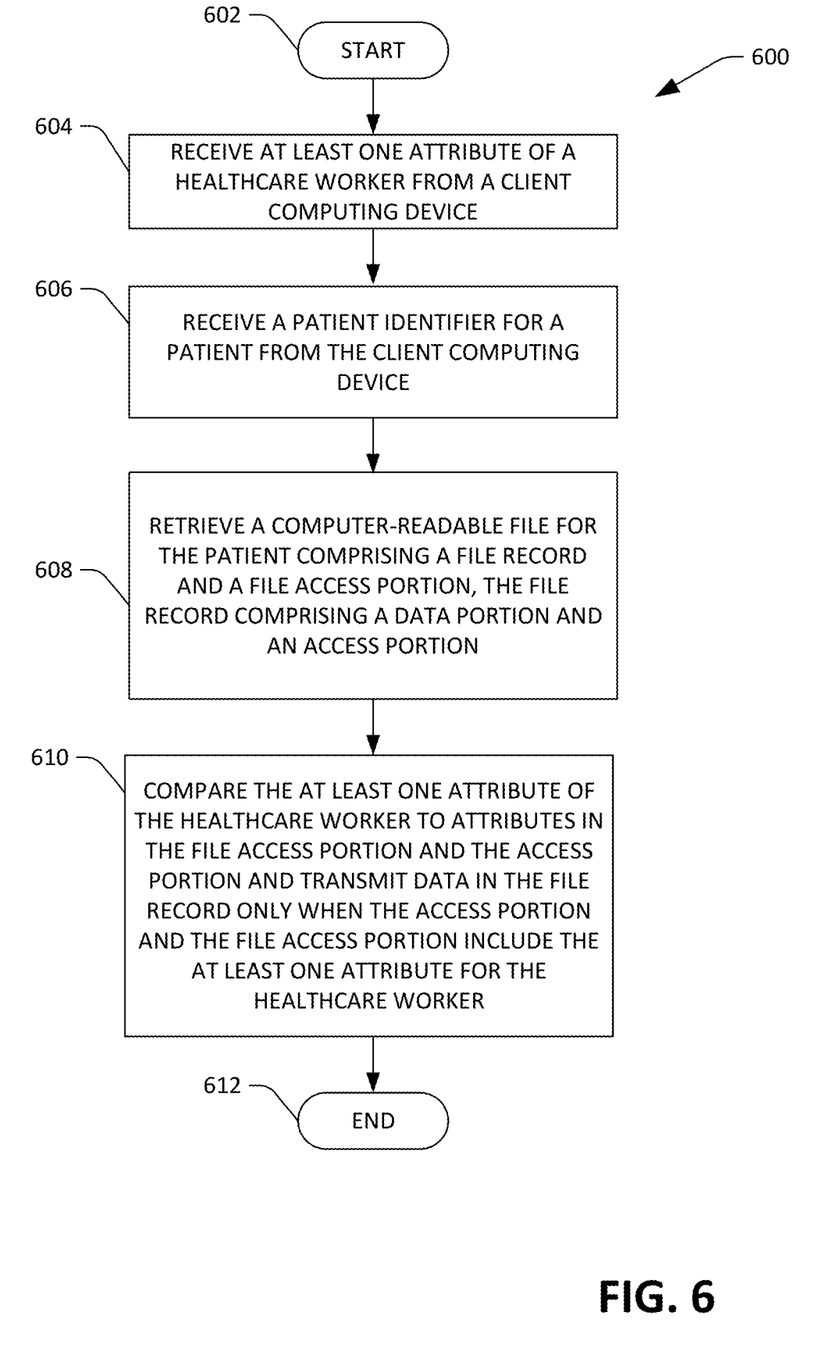
FIG. 6 is a flow diagram that illustrates an exemplary methodology executed at a computing system for facilitating digital rights management of healthcare records.
Figure 7:
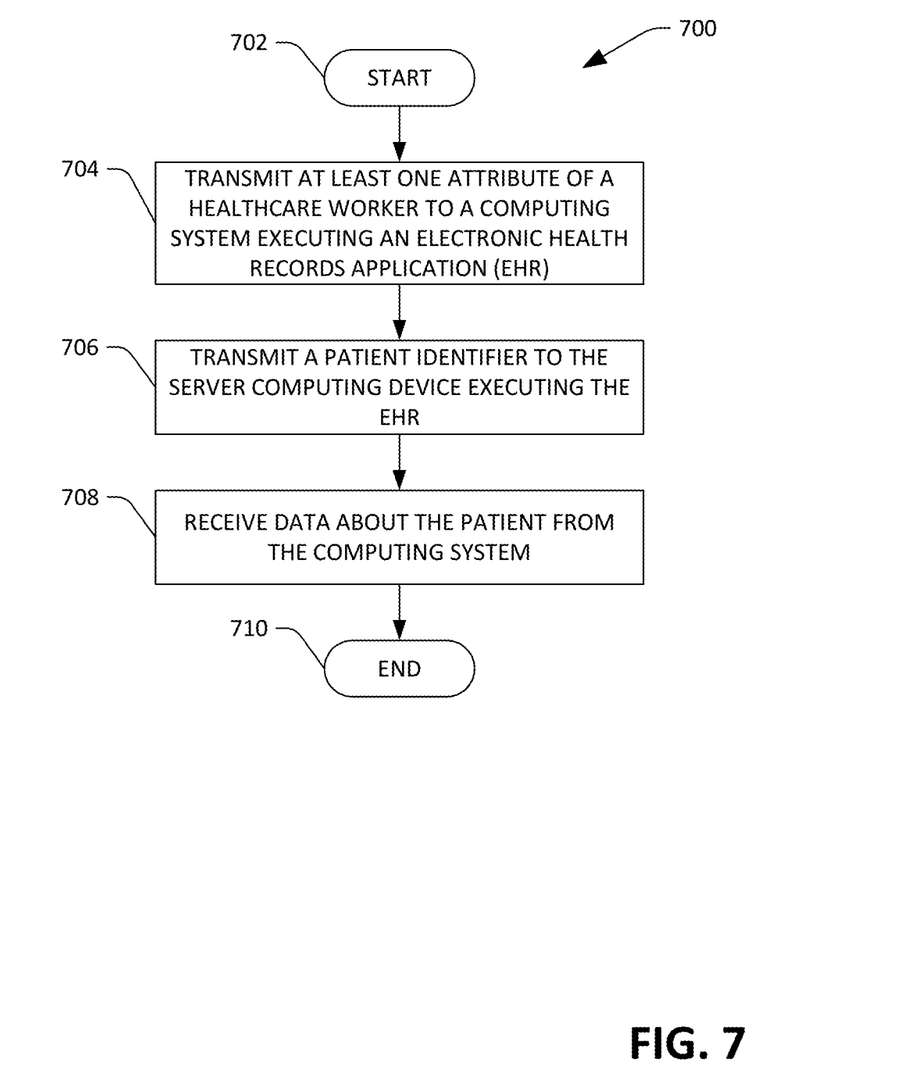
FIG. 7 is a flow diagram that illustrates an exemplary methodology executed at a client computing device for facilitating digital rights management of healthcare records.

FIGS. 6 and 7 illustrate exemplary methodologies relating to facilitating digital rights management for patient health records. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 6, a methodology executed at a computing system that facilitates digital rights management for patient health records is illustrated. The methodology 600 begins at 602, and at 604 the computing system receives at least one attribute of a healthcare worker from a client computing device. Subsequently, at 606, the computing system receives a patient identifier for a patient. At 608, responsive to receiving the patient identifier, the computing system retrieves a computer-readable file for the patient. As described above, the computer-readable file comprises a plurality of file records and a file access portion. The file access portion comprises an attribute of healthcare workers who have permission to access the computer-readable file. The plurality of file records includes a file record comprising data about the patient and an access portion. The access portion comprises an attribute of healthcare workers that have permission to access the file record.

At 610, the computing system compares the at least one attribute of the healthcare worker to the attribute in the file access portion. The computing system also compares the at least one attribute of the healthcare worker to the attribute in the access portion of the file record. The computing system transmits the data in the data portion of the file record only when both the file access portion and the access portion of the file record include the at least one attribute of the healthcare worker. The methodology 600 concludes at 612.

Turning now to FIG. 7, a methodology executed at a client computing device that facilitates digital rights management for patient health records is illustrated. The methodology 700 begins at 702, and at 704 the client computing device transmits at least one attribute of a healthcare worker to a computing system executing an EHR. Subsequently, at 706, the client computing device transmits a patient identifier for a patient to the computing system. As described above, the computing system retrieves a computer-readable file for the patient and identifies file records in the computer-readable file that the healthcare worker has permission to access based on the at least one attribute of the healthcare worker received from the client computing device, an attribute in the file access portion, and an attribute in the access portion of the file record. At 708, the client computing device receives patient data from the computing system. The patient data includes only data from file records which include the at least one attribute of the healthcare worker. The methodology 700 concludes at 710.

Figure 8:
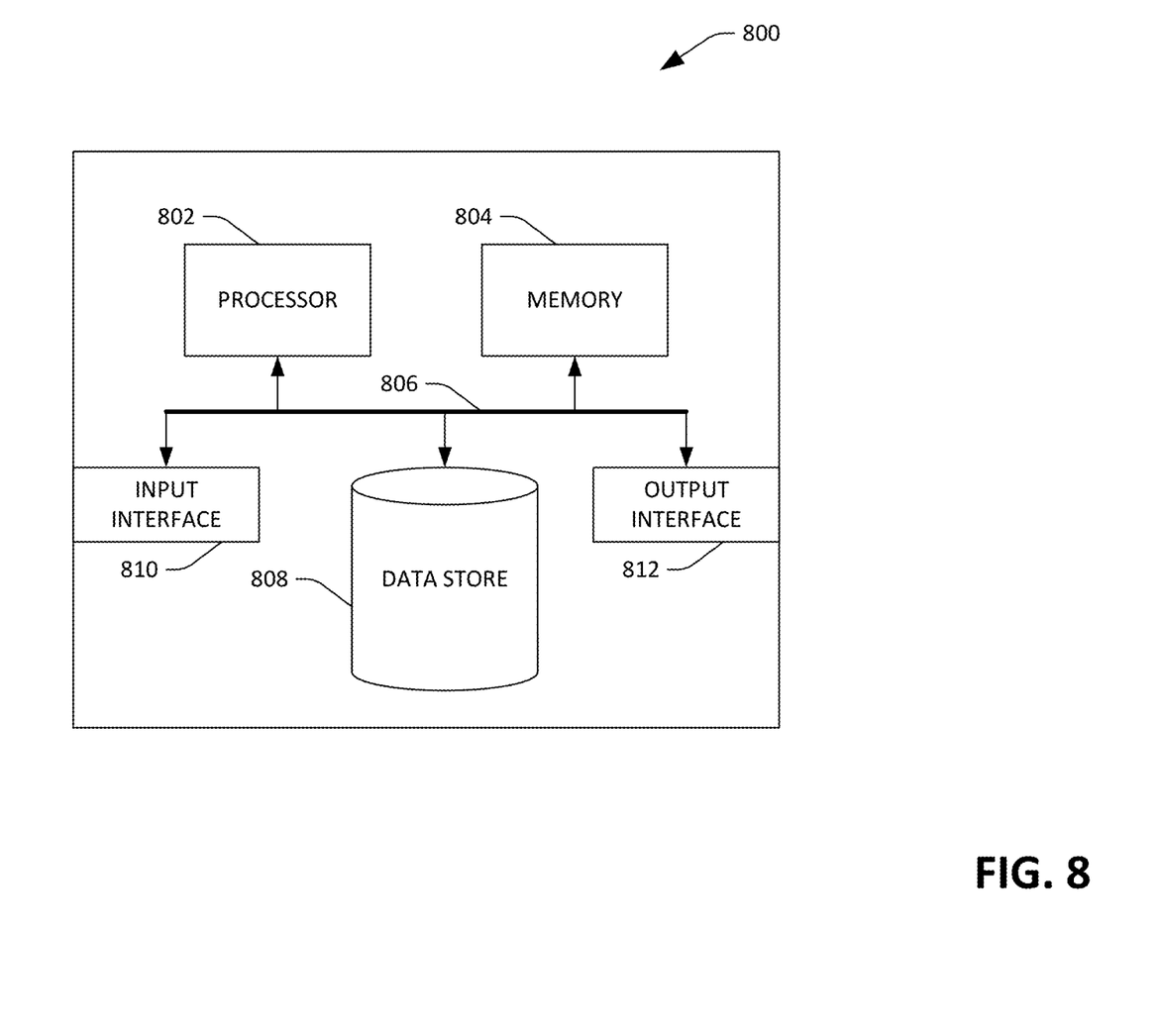
FIG. 8 is an exemplary computing system.

Referring now to FIG. 8, a high-level illustration of an exemplary computing device 800 that can be used in accordance with the systems and methodologies disclosed herein is illustrated. For instance, the computing device 800 may be used in a system that facilitates digital rights management for patient health records. By way of another example, the computing device 800 can be used in a system that transmits patient health records only when access requirements for the patient health records are met. The computing device 800 includes at least one processor 802 that executes instructions that are stored in a memory 804. The instructions may be, for instance, instructions for implementing functionality described as being carried out by one or more components discussed above or instructions for implementing one or more of the methods described above. The processor 802 may access the memory 804 by way of a system bus 806. In addition to storing executable instructions, the memory 804 may also store patient health records.

The computing device 800 additionally includes a data store 808 that is accessible by the processor 802 by way of the system bus 806. The data store 808 may include executable instructions, patient health records, etc. The computing device 800 also includes an input interface 810 that allows external devices to communicate with the computing device 800. For instance, the input interface 810 may be used to receive instructions from an external computer device, from a user, etc. The computing device 800 also includes an output interface 812 that interfaces the computing device 800 with one or more external devices. For example, the computing device 800 may display text, images, etc. by way of the output interface 812.

It is contemplated that the external devices that communicate with the computing device 800 via the input interface 810 and the output interface 812 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 800 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 800 may be a distributed system. Thus, for instance, several devices may be in communication by way of a network connection and may collectively perform tasks described as being performed by the computing device 800.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A computing system comprising:
a processor; and
memory that stores an electronic health records application (EHR) that, when executed by the processor, causes the processor to perform acts comprising:
receiving at least one attribute of a healthcare worker from a client computing device executing a client EHR;
receiving a patient identifier for a patient from the client computing device;
responsive to receiving the patient identifier, retrieving a computer-readable file for the patient based on the patient identifier, wherein the computer-readable file for the patient comprises:
a plurality of file records, the plurality of file records comprising a file record including a data portion and an access portion, the access portion in the file record comprises an attribute, wherein access to data in the data portion is restricted to healthcare workers who have the attribute in the access portion, wherein the attribute in the access portion does not include the at least one attribute of the healthcare worker;

a file access portion including the attribute and a date associated with the attribute, wherein access to the computer-readable file is restricted to healthcare workers who have the attribute in the file access portion; and a timestamp indicative of when the file record was created;

responsive to retrieving the computer-readable file for the patient, comparing the at least one attribute of the healthcare worker to the attribute included in the file access portion, comparing the at least one attribute of the healthcare worker to the attribute included in the access portion of the file record, and transmitting the data portion of the file record to the client computing device only when the file access portion and the access portion include the at least one attribute of the healthcare worker and only when the timestamp is after the date in the file access portion;

receiving an indication from the client computing device that access to the file record has been granted to the healthcare worker; and responsive to receiving the indication, modifying the access portion of the file record to include the at least one attribute of the healthcare worker.

2. The computing system of claim 1, the acts further comprising:

subsequent to receiving the at least one attribute of the healthcare worker from the client computing device, retrieving a second attribute of the healthcare worker by executing a search over a data store accessible to the EHR based on the at least one attribute of the healthcare worker.

3. The computing system of claim 1, the acts further comprising:

when the file access portion does not include the at least one attribute of the healthcare worker, transmitting a message to the client computing device indicating that the healthcare worker lacks permission to access the computer-readable file.

4. The computing system of claim 1, the acts further comprising:

when the access portion in the file record does not include the at least one attribute of the healthcare worker, transmitting a message to the client computing device indicating that the healthcare worker lacks permission to access the file record in the computer-readable file.

5. The computing system of claim 1, wherein the at least one attribute of the healthcare worker is an identity of a healthcare organization to which the healthcare worker belongs, wherein the attribute in the file access portion is the identity of the healthcare organization.

6. The computing system of claim 1, wherein the at least one attribute of the healthcare worker is an identifier for the healthcare worker, wherein the attribute in the access portion of the file record is the identifier for the healthcare worker.

7. The computing system of claim 1, wherein the access portion further comprises a second attribute, the acts further comprising:

receiving an indication from the client computing device that the patient wishes to remove access to the file record for persons possessing the second attribute;

responsive to receiving the indication, removing the second attribute from the access portion.

8. The computing system of claim 1, wherein the computer-readable file is encrypted, the acts further comprising:

prior to transmitting the data portion of the file record to the client computing device, decrypting the computer-readable file.

9. The computing system of claim 1, wherein the computer-readable file is compressed, the acts further comprising:

prior to transmitting the data portion of the file record to the client computing device, decompressing the computer-readable file.

10. A method executed by a computing system executing an electronic health records application (EHR), the method comprising:

receiving at least one attribute of a healthcare worker from a client computing device executing a client EHR;

receiving a patient identifier for a patient from the client computing device;

responsive to receiving the patient identifier, retrieving a computer-readable file for the patient based on the patient identifier, wherein the computer-readable file for the patient comprises:

a plurality of file records, the plurality of file records comprising a file record including a data portion and an access portion, the access portion in the file record comprises an attribute, wherein access to data in the data portion is restricted to healthcare workers who have the attribute in the access portion, wherein the attribute in the access portion does not include the at least one attribute of the healthcare worker; and a file access portion, the file access portion comprises a second attribute, wherein access to the computer-readable file is restricted to healthcare workers who have the second attribute in the file access portion;

responsive to retrieving the computer-readable file for the patient, comparing the at least one attribute of the healthcare worker to the second attribute included in the file access portion, comparing the at least one attribute of the healthcare worker to the attribute included in the access portion of the file record, and transmitting the data portion of the file record to the client computing device only when the file access portion and the access portion include the at least one attribute of the healthcare worker;

receiving an indication from the client computing device that access to the file record has been granted to the healthcare worker; and responsive to receiving the indication, modifying the access portion of the file record to include the at least one attribute of the healthcare worker.

11. The method of claim 10, wherein the computer-readable file further includes a timestamp indicative of when the file record was created, wherein the file access portion further includes a date associated with the second attribute in the file access portion, the method further comprising:

transmitting the data portion of the file record to the client computing device only when the timestamp is after the date in the file access portion.

12. The method of claim 10, wherein the computer-readable file further includes a timestamp indicative of when the file record was created, wherein the file access portion further includes a date associated with the second attribute in the file access portion, the method further comprising:
   transmitting the data portion of the file record to the client computing device only when the timestamp is before the date in the file access portion.

13. The method of claim 10, wherein the at least one attribute of the healthcare worker is an identity of a healthcare organization to which the healthcare worker belongs, wherein the second attribute in the file access portion is the identity of the healthcare organization.

14. The method of claim 10, wherein the at least one attribute of the healthcare worker is an identifier for the healthcare worker, wherein the attribute in the access portion in the file record is the identifier for the healthcare worker.

15. The method of claim 10 further comprising:
   when the file access portion does not include the at least one attribute of the healthcare worker, transmitting a message to the client computing device indicating that the healthcare worker lacks permission to access the computer-readable file.

16. A non-transitory computer-readable storage medium comprising instructions that, when executed by a processor, cause the processor to perform acts comprising:
   receiving at least one attribute of a healthcare worker from a client computing device;
   receiving a patient identifier for a patient from the client computing device;
   responsive to receiving the patient identifier, retrieving a computer-readable file for the patient by executing a search based on the patient identifier over a data store comprising computer readable files for a plurality of patients, wherein the computer-readable file for the patient comprises:
      a plurality of file records, the plurality of file records comprising a file record, the file record including a data portion and an access portion, an access portion in the file record comprises an attribute, and further wherein access to data in the data portion is restricted to healthcare workers who have the attribute in the access portion, wherein the attribute in the access portion does not include the at least one attribute of the healthcare worker; and
      a file access portion, the file access portion comprises a second attribute, wherein access to the computer-readable file is restricted to healthcare workers who have the second attribute in the file access portion;
   responsive to retrieving the computer-readable file for the patient, comparing the at least one attribute of the healthcare worker to the second attribute in the file access portion, comparing the at least one attribute of the healthcare worker to the attribute included in the access portion of the file record, and transmitting the data portion of the file record to the client computing device only when the file access portion and the access portion include the at least one attribute of the healthcare worker;
   receiving an indication from the client computing device that access to the file record has been granted to the healthcare worker; and
   responsive to receiving the indication, modifying the access portion of the file record to include the at least one attribute of the healthcare worker.

17. The non-transitory computer-readable storage medium of claim 16, wherein the access portion further comprises a third attribute, the acts further comprising:
   receiving an indication from the client computing device that the patient wishes to restrict access to the file record for persons possessing the third attribute; and
   responsive to receiving the indication, removing the third attribute from the access portion.

18. The non-transitory computer-readable storage medium of claim 16, wherein the computer-readable file further includes a timestamp indicative of when the file record was created, wherein the file access portion further includes a date associated with the second attribute in the file access portion, the acts further comprising:
   transmitting the data portion of the file record to the client computing device only when the timestamp is before the date in the file access portion.

* * * * *